US011166798B2

(12) United States Patent
Eisele et al.

(10) Patent No.: US 11,166,798 B2
(45) Date of Patent: *Nov. 9, 2021

(54) INJECTOR FOR INJECTING PELLETS

(71) Applicant: Henke-Sass, Wolf GmbH, Tuttlingen (DE)

(72) Inventors: Melanie Eisele, Wurmlingen (DE); Stefan Knefel, Steisslingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 247 days.

This patent is subject to a terminal disclaimer.

(21) Appl. No.: 16/412,399

(22) Filed: May 14, 2019

(65) Prior Publication Data
US 2019/0262115 A1    Aug. 29, 2019

Related U.S. Application Data

(63) Continuation of application No. 15/068,532, filed on Mar. 11, 2016, now Pat. No. 10,405,955.

(30) Foreign Application Priority Data

Mar. 13, 2015    (DE) .......................... 102015103749.1

(51) Int. Cl.
*A61D 7/00* (2006.01)
*A61M 37/00* (2006.01)
*A61M 3/02* (2006.01)

(52) U.S. Cl.
CPC ........... *A61D 7/00* (2013.01); *A61M 37/0069* (2013.01); *A61M 3/0266* (2013.01); *A61M 2202/06* (2013.01)

(58) Field of Classification Search
CPC ............ A61M 37/009; A61M 2202/06; A61M 3/0266; A61M 37/0069; A61D 7/00
See application file for complete search history.

(56) References Cited

U.S. PATENT DOCUMENTS

| | | | | |
|---|---|---|---|---|
| 3,924,788 A | * | 12/1975 | Furutu | ..................... B65C 7/005 227/67 |
| 4,077,406 A | * | 3/1978 | Sandhage | ......... A61M 37/0069 604/61 |
| 4,154,239 A | * | 5/1979 | Turley | .............. A61M 37/0069 604/61 |
| 4,465,191 A | * | 8/1984 | Darbo | ................ B65D 83/0445 206/535 |

(Continued)

*Primary Examiner* — Jenna Zhang
(74) *Attorney, Agent, or Firm* — Skaar Ulbrich Macari, P.A.

(57) ABSTRACT

An injector for injecting pellets includes a main body, a delivery opening which is formed on the main body and to which a hollow-bore needle can be connected and a magazine guide formed in the main body for a magazine which, for accommodating the pellets, comprises several barrels. Each barrel includes a hollow cylindrical compartment with an open front end and an open rear end. The magazine guide brings the magazine, barrel by barrel, into an injection position, in which a plunger of the injector can be introduced into the barrel via the rear end of the barrel positioned in the injection position and moved in the direction of the delivery opening in order to deliver the pellet provided in the barrel via the delivery opening. A drawer is formed in the main body for accommodating a replacement hollow-bore needle.

20 Claims, 5 Drawing Sheets

(56) References Cited

U.S. PATENT DOCUMENTS

| | | | | |
|---|---|---|---|---|
| 4,762,515 | A * | 8/1988 | Grimm | A61M 37/0069 |
| | | | | 604/61 |
| 5,608,940 | A * | 3/1997 | Panyon, Jr. | A46B 11/001 |
| | | | | 132/311 |
| 5,639,006 | A * | 6/1997 | Kim | B65C 7/005 |
| | | | | 227/67 |
| 5,813,589 | A * | 9/1998 | Kim | B65C 7/005 |
| | | | | 227/67 |
| 6,258,056 | B1 * | 7/2001 | Turley | A61M 37/0069 |
| | | | | 604/110 |
| 2002/0162565 | A1 * | 11/2002 | Sebban | A45D 40/221 |
| | | | | 132/293 |

* cited by examiner

INJECTOR FOR INJECTING PELLETS

PRIORITY

This application is a continuation of U.S. patent application Ser. No. 15/068,532, filed Mar. 11, 2016, which claims the benefit of German Patent Application No. 102015103749.1, filed on Mar. 13, 2015, all of which are hereby incorporated herein by reference in their entirety.

FIELD

The present invention relates to an injector for injecting pellets.

BACKGROUND

With pellet injectors there is the difficulty that the hollow-bore needle connected to a delivery opening of the injector frequently becomes worn-out or breaks off. This can occur e.g. when injecting pellets into animals. As such injections are frequently carried out e.g. in the stable, a great deal of time is then wasted in obtaining a replacement hollow-bore needle and connecting it to the delivery opening in exchange for the worn-out or broken-off hollow-bore needle.

SUMMARY

An object of the invention is therefore to provide an injector for injecting pellets, with which the above-noted difficulties can be overcome as completely as possible.

The disclosure includes an injector (in particular by an injector for the veterinary field) for injecting pellets, wherein the injector comprises a main body, a delivery opening which is formed on the main body and to which a hollow-bore needle can be connected and a magazine guide formed in the main body for a magazine which, for accommodating the pellets, comprises several barrels which in each case comprise a hollow cylindrical compartment with an open front end and an open rear end, wherein the magazine guide brings the magazine, barrel by barrel, into an injection position, in which a plunger of the injector can be introduced into the barrel via the rear end of the barrel positioned in the injection position and moved in the direction of the delivery opening in order to deliver the pellet provided in the barrel via the delivery opening and wherein, in the main body, a drawer is formed for accommodating a replacement hollow-bore needle.

Through the provision of the drawer, at least one replacement hollow-bore needle can always be carried with the injector, with the result that during use of the injector, if the hollow-bore needle currently connected to the delivery opening breaks off or is worn-out, the replacement hollow-bore needle can be removed from the drawer and connected to the delivery opening in exchange for the broken-off or worn-out hollow-bore needle.

The drawer can of course also be formed such that it can accommodate several replacement hollow-bore needles.

The drawer can be formed such that in the pushed-in state it closes flush with the main body. The drawer can thus be pushed completely into the main body.

The drawer can comprise a spring element which, when the drawer is pulled out, raises the hollow-bore needle (or hollow-bore needles) situated in the drawer. In particular, the spring element can be arranged in the area of the bottom or be formed as part of the bottom. By means of the spring element, when the drawer is retracted, the replacement hollow-bore needle situated in the drawer can be held in a tensioned position (e.g. by means of a corresponding guide in the main body).

In the wall of the main body at least one (e.g. rectilinear) guide for the drawer can be formed, wherein a knob of the drawer, which can be actuated by the user from the outside, projects into the guide. In particular, a guide for a knob of the drawer can be provided on both sides of the main body.

In the main body at least one guide bar can be formed, which serves to guide the drawer. In particular an upper and lower guide bar can be provided, between which the drawer is guided. The upper guide bar can likewise serve to hold the replacement hollow-bore needle in the tensioned position, by exerting a force in the direction of the bottom of the drawer.

Furthermore, the drawer can be pulled out of the main body in a direction away from the delivery opening.

Furthermore, the drawer can be formed such that in the pushed-in state it is secured against an accidental slipping out or moving out. The securing element can be formed e.g. such that, by pressing on the end of the drawer in the direction of the main body, the securing element is released and the drawer is then moved, preferably automatically, (at least partially) in the outward direction. This can be realized e.g. by a corresponding spring, with the result that the protruding end of the drawer, if the latter does not come out completely, can then be grasped and the drawer can thus be pulled out.

The injector can include the magazine inserted into the magazine guide. In particular the magazine can be formed in such a way that the cross section of the compartment as well as of the front end is selected such that a pellet to be accommodated can be accommodated, and the cross section of the rear end is smaller than the pellet to be accommodated, with the result that the pellet cannot be extracted from the compartment via the rear end, wherein the magazine further comprises a cover for closing the front end, wherein the cover comprises a dispensing opening which, in the closed state, is positioned in front of the front end and has a cross section which is selected such that the pellet can pass through the dispensing opening, and wherein at least one bar projecting into the dispensing opening is provided which, when the cover is closed, prevents the pellets from accidentally falling out and, when subjected to a predetermined force, can be bent outwards such that the pellet can be delivered through the dispensing opening.

As the magazine according to the invention comprises the described cover with the bar projecting into the dispensing opening, the compartment can be easily filled if the cover is not provided, and the pellet can be securely accommodated and stored if the front end of the compartment is closed with the cover.

The outward bending can be e.g. a pure bending, a kinking or a combination of bending and kinking. After delivery of the pellet, the bent bar can return fully to its original position before the bending. However, it is also possible for the bent bar to only partially return to its original position.

In particular two bars projecting into the dispensing opening can be provided. The two bars can lie opposite each other and the distance between their free ends facing each other can be smaller than the corresponding dimension of the pellets.

Due to the at least one bar in its original position, in which it projects into the dispensing opening, there is a free area in the dispensing opening through which the pellet does not pass.

The bar (or bars) is in particular formed as an elastic bar.

By cross section of the rear end is meant in particular the cross-sectional shape and/or the cross-sectional area. It is important that the cross section of the rear end is selected such that the pellet does not pass through. In particular the cross section of the rear end is selected such that the plunger of the injector can be introduced into the compartment through the rear end, in order to be able to deliver the at least one pellet via the dispensing opening of the closed cover.

The cover can be linked to the barrel via a hinge. In particular the cover can be connected to the barrel in such a way that it cannot be lost. The hinge can for example be formed as a film hinge.

The compartment of the barrel preferably extends in a straight line.

The disclosure further includes a security device, which secures the cover against accidental opening in the closed state. The security device can comprise a detent connection between cover and barrel. In particular a detent nose can be provided on the barrel and an associated detent recess can be provided on the cover.

The security device can be formed such that repeated opening and closing of the cover is possible. Alternatively the security device can be formed such that the cover, once closed, can only be opened accompanied by at least partial destruction. By this is meant in particular that, after opening, the cover can no longer be closed such that it is secured against accidental opening.

The magazine according to certain disclosed embodiment can comprise at least two, three or more of the barrels, wherein the hollow cylindrical compartments run parallel to each other. The front ends of the compartments preferably lie next to each other along a straight line.

In particular the cover for each barrel can comprise one of the dispensing openings, with the result that, in the closed state, one of the dispensing openings is positioned in front of each front end.

The front ends of the compartments can open into an end plate connecting the barrels. In this case it is preferred that the cover is linked to the end plate.

The barrels can be firmly connected to each other. In particular the at least one barrel and the cover can be formed as a one-piece magazine.

The magazine can for example be an injection-moulded part and thus can be produced in a simple manner with the desired precision and in the desired numbers.

The hollow cylindrical compartments of the barrels are preferably formed identical. In particular the cross section of the compartments can be constant along the longitudinal direction of the barrels. A circular cross section is preferred. However, any other cross-sectional shape is also possible. For example the cross section can be polygonal.

The pellets are preferably pellets containing a medicament. Each compartment can accommodate one or more pellets. The pellets can also be formed as tablets, compacts, or in some other way.

It is also possible for the pellets to be formed as implants. It is thus possible to introduce an implant, e.g. into an animal. The implant can be a medical implant and/or an implant with which e.g. a clear identification of the corresponding animal is possible. Thus the implant can for example comprise wirelessly readable unique information, such as e.g. a serial number.

The pellets are preferably in a solid form, with the result that they can transfer the necessary force to the at least one bar for the bending.

The pellet can in particular be formed cylindrical. The cross-sectional shape of the compartment is preferably adapted to the usual cross-sectional shape of the pellet to be accommodated. If the pellet is formed e.g. as a circular cylinder, the cross section of the compartment can also be circular. However, a different shape of the compartment is also possible. For example, in the case of a pellet with a circular cross section, the cross section of the compartment can be elliptical or polygonal or have another shape.

The magazine according to the invention is in particular formed as a disposable item. The magazine according to the invention can also be formed as a reusable magazine.

The magazine according to the invention is preferably produced from plastic material.

The injector can contain an actuation device for actuating the plunger. The actuation device can comprise an actuation element (such as e.g. a lever or a button) that can be operated from the outside and a drive unit for the plunger. After actuation of the actuation element, the plunger is moved by means of the drive unit and the magazine is then preferably further moved around a barrel. The drive unit can bring about the movement of the plunger mechanically, pneumatically and/or electrically. The same applies to the movement of the magazine by means of the magazine guide.

It is understood that the features mentioned above and those yet to be explained below can be used, not only in the stated combinations, but also in other combinations or alone, without departing from the scope of the present invention.

Figure 1:
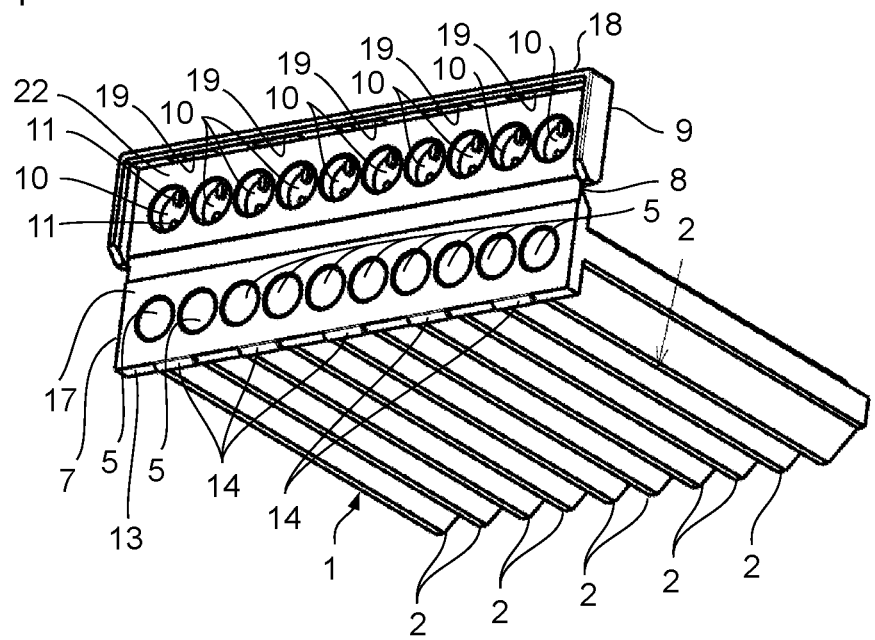
FIG. 1 is a perspective view of an embodiment of the magazine according to the invention with opened cover.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

Figure 5:
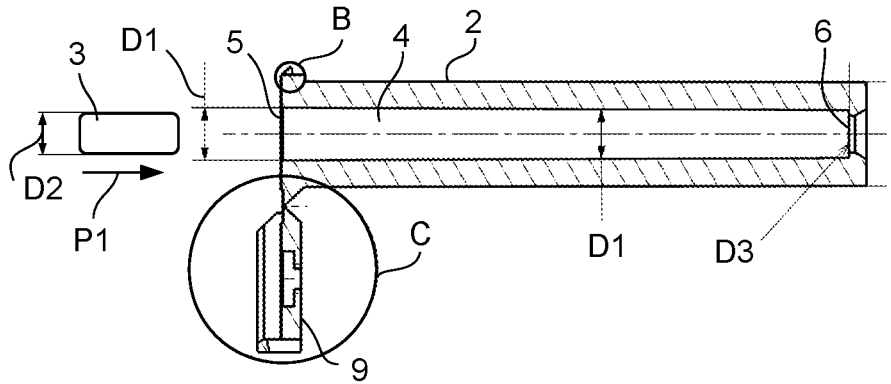
FIG. 5 is a sectional view of the magazine along the sectional line A-A of FIG. 3.
Figure 6:
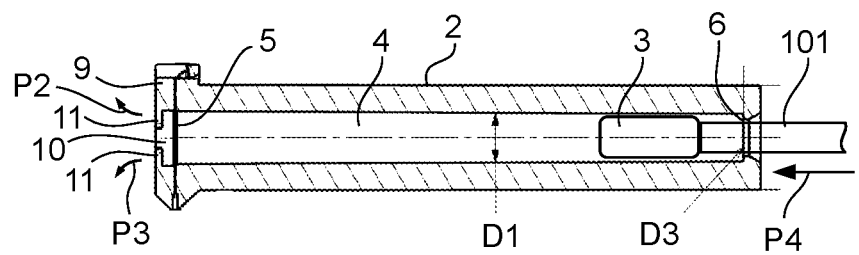
FIG. 6 is a sectional view according to FIG. 5, but in which the cover, unlike in FIG. 5, is in its closed position.

In the embodiment shown in FIG. 1 the magazine 1 according to the invention comprises several barrels 2 (here for example ten barrels 2) for accommodating pellets 3 (one pellet 3 is in each case shown schematically in the sectional representations of FIGS. 5 and 6).

The magazine 1 according to the invention serves for use in an injector 100, in order to inject the pellets from the barrels 2 into an animal for the administration of at least one medicament which is contained in the pellets 3, as described in further detail below.

The barrels 2 are aligned parallel to each other and in each case comprise a hollow cylindrical compartment 4 with an open front end 5 and an open rear end 6, as can be seen in particular from the representation according to FIGS. 1, 3, 4 and 9 as well as the sectional representations in FIGS. 5 and 6.

The barrels 2 are connected to each other and their front ends 5 lie in an end plate 7 to which a cover 9 is linked via a hinge 8 (for example a film hinge). In the representations of FIGS. 1, 3 to 5 and 9 the cover 9 is shown in an opened position and in the representation according to FIG. 6 the cover 9 is shown in a closed position, as described in further detail below.

For each barrel 2 the cover 9 comprises a dispensing opening 10, which is positioned, in the closed position of the cover 9, in front of the front end 5 of the corresponding barrel 2.

The hollow cylindrical compartments 4 of the barrels 2 here have a circular cross section with a diameter D1 (FIG. 5), wherein the diameter D1 is selected to be greater than the diameter D2 of the pellets 3, with the result that pellets 3 can be accommodated. The hollow cylindrical compartments 4 are formed such that they extend in a straight line and have a constant cross section. Only the open rear end 6 has a smaller diameter D3 than the diameter D1 of the hollow cylindrical compartment 4. This smaller diameter D3 is selected such that it is smaller than the corresponding diameter D2 of the pellets 3 to be accommodated, with the result that the pellets 3 cannot be extracted from the compartment 4 via the rear end 6.

The dispensing openings 10 in the cover 9 have in each case a diameter D4 (FIG. 8) which is greater than the diameter D2 of the pellets. In particular the diameter D4 can be equal to the diameter D1. In addition, each dispensing opening 10 comprises at least one bar 11 projecting inwards (e.g. radially inwards) into the dispensing opening 10. In the embodiment shown here, each dispensing opening 10 comprises two bars 11 opposite each other, the dimensions of which are selected such that the free diameter D5 (distance between the front ends 12 of the bars 11 facing each other) is smaller than the corresponding extent D2 of the pellets 3. It is thereby achieved that, when the cover 9 is opened as indicated schematically in FIG. 5 by an arrow P1, the barrels 2 can be filled with pellets 3 via the front ends 5. When the cover 9 is closed, the pellets 3 cannot then fall out of the barrels 2 via the front end 5, as this is prevented by the bars 11 of the dispensing openings 10 positioned in front of the front ends 5. The pellets 3 also cannot be extracted from the barrels 2 via the rear end 6, as the diameter D3 of the rear ends 6 is smaller than the corresponding extent D2 of the pellets 3.

The bars 11 are elastic and dimensioned such that they are bent outwards by the pellets 3 (as indicated by the arrows P2 and P3 in FIG. 6) when a predetermined force is exceeded, with the result that the pellets 3 can then be delivered via the front ends 5 and the dispensing openings 10.

Figure 10:
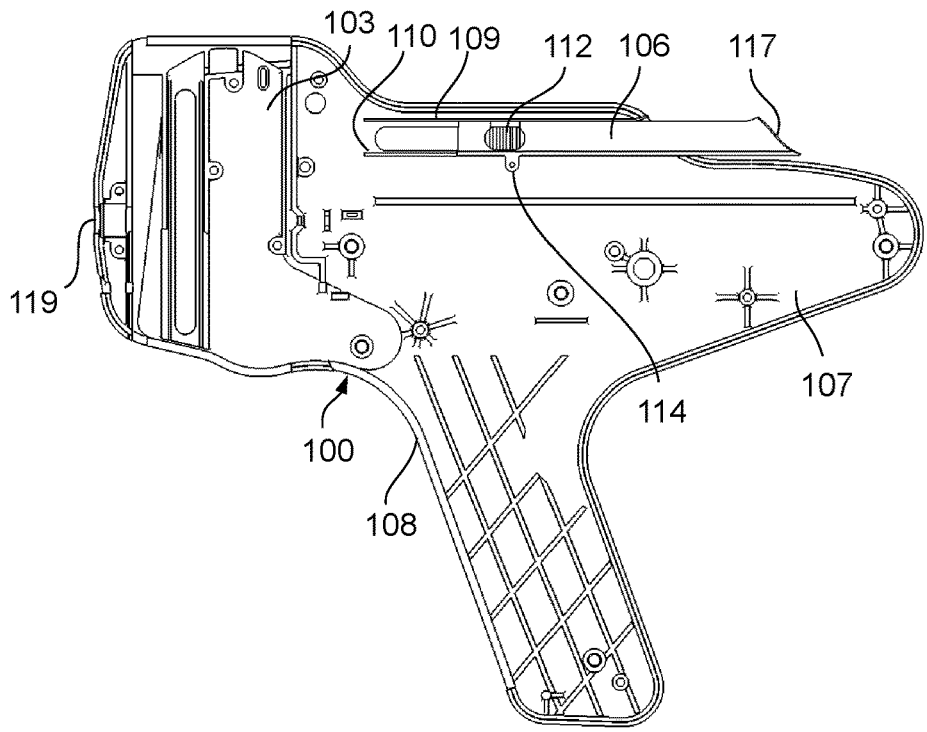
FIG. 10 is a view of the rear shell of the injector according to FIG. 2 together with the drawer arranged in the housing.
Figure 11:
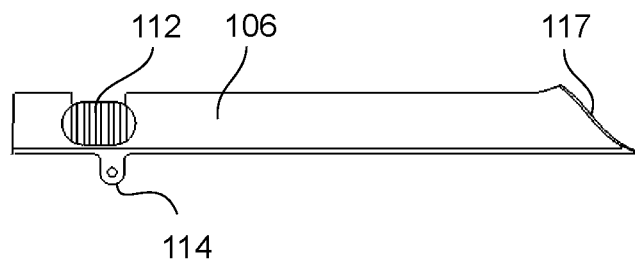
FIG. 11 is a side view of the drawer of FIG. 10.
Figure 12:
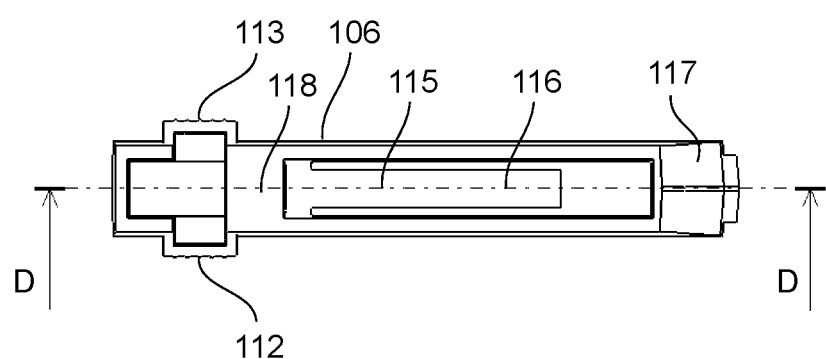
FIG. 12 is a view of the drawer from above according to FIG. 11.
Figure 13:
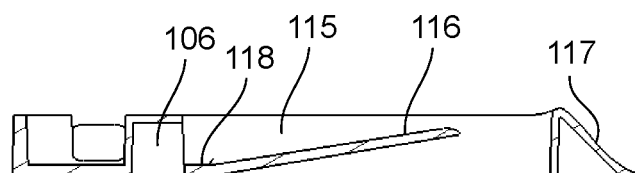
FIG. 13 is a sectional view of the drawer along the sectional line D-D in FIG. 12.

The delivery is achieved in the case of an injector 100 in that a plunger 101 (or a rod 101) of the injector 100, as indicated in FIG. 6, is introduced into the hollow cylindrical compartment 4 via the open rear end 6 of the corresponding barrel 2 and is delivered during a further movement in the direction indicated by the arrow P4, via the front end 5 and the dispensing opening 10 and e.g. a hollow-bore needle 102 of the injector 100 (FIG. 2), which is connected to a delivery opening 119 of the injector 100 (FIG. 10). The diameter D3 of the open rear end 6 is designed such that an unchecked introduction of the plunger 101 is possible.

Figure 2:
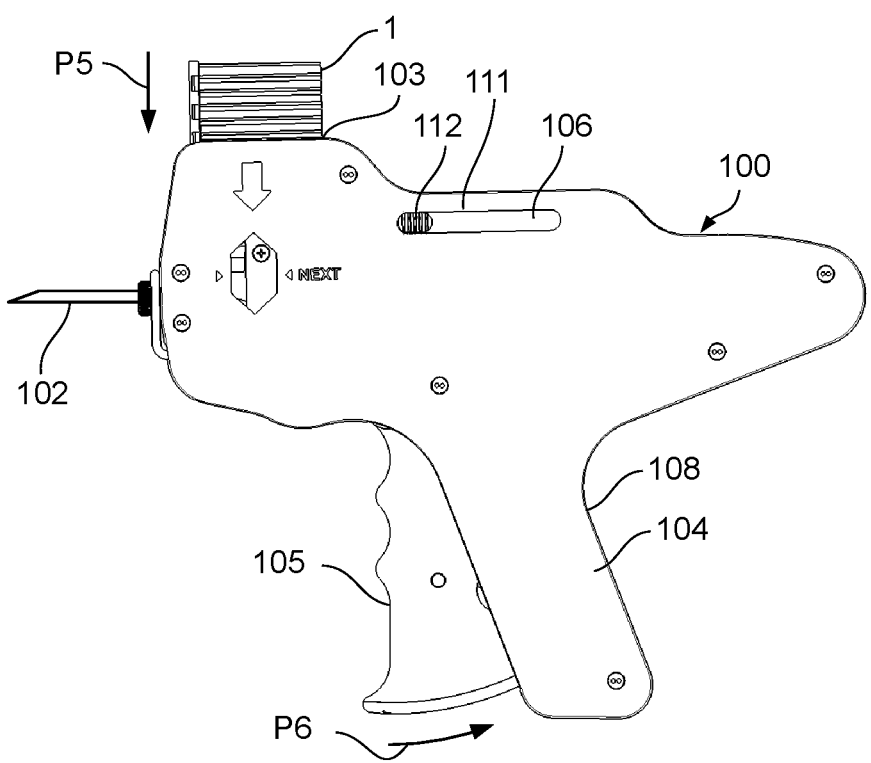
FIG. 2 is an injector together with the magazine according to the invention.
Figure 3:
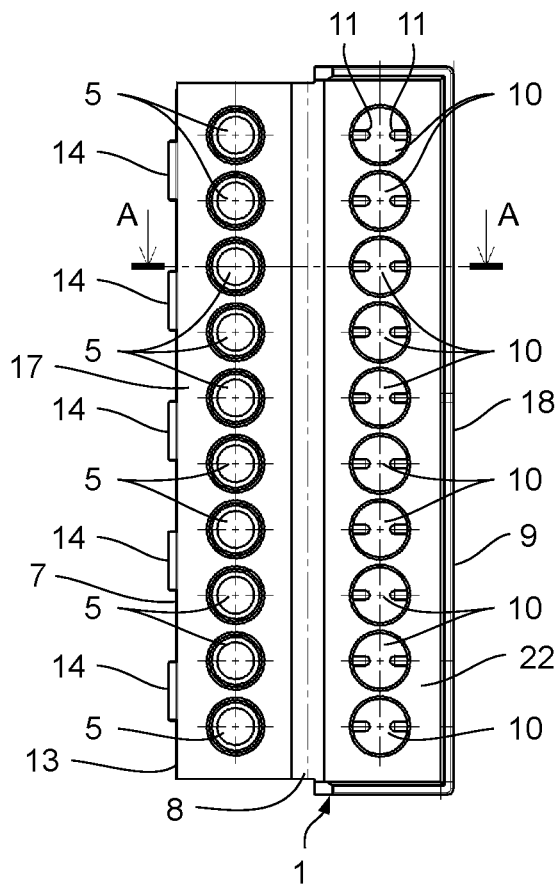
FIG. 3 is a view from above of the magazine according to FIG. 1 with opened cover.
Figure 4:
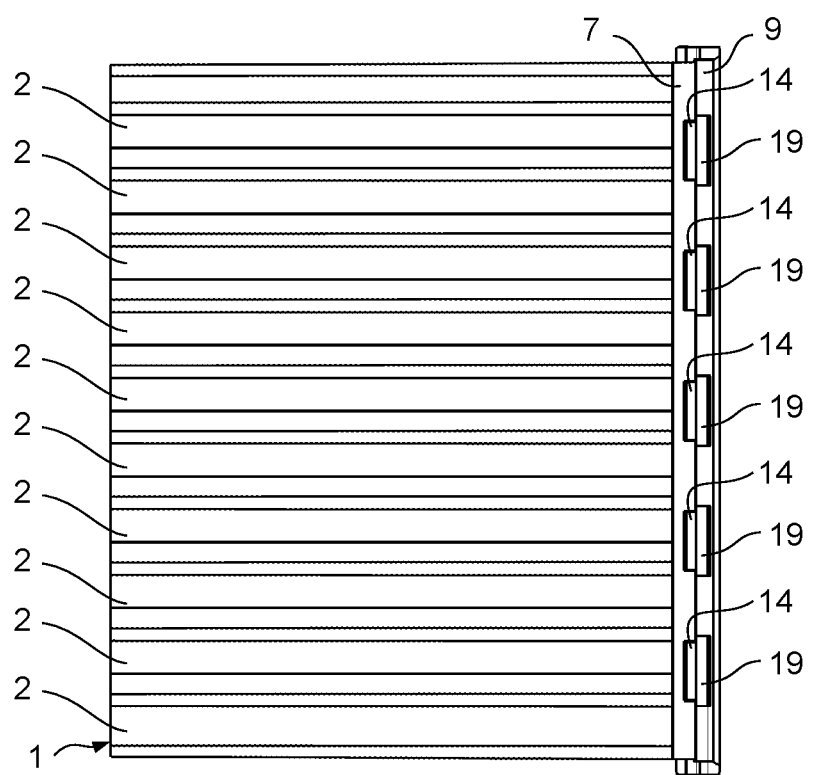
FIG. 4 is a side view of the magazine according to FIG. 1 with opened cover.

As is usual with such injectors 100, a magazine guide 103 (FIGS. 2 and 10) is provided, with which the magazine 1 according to the invention can be moved in the direction according to the arrow P5 in each case stepwise such that in each case the next barrel 2 with its pellets 3 provided in the compartment 4 is positioned between the plunger 101 and the hollow-bore needle 102 in an extraction position, which can also be called the injection position, with the result that for injection the plunger 101 can deliver the pellets 3 through the hollow cylindrical compartment 4 and the hollow-bore needle 102 in the manner described. For this, the injector 1, as indicated in FIG. 2, can be formed like a pistol with a grip 104 and a swivellable lever 105, wherein when the lever 105 is swivelled in the direction of the arrow P6 the injection of the pellets 3 is carried out through the described movement of the plunger 101 and when the lever swings back into the position shown in FIG. 2 the magazine 1 is moved downwards by one barrel 2 in the direction of the arrow P5, with the result that, at the next actuation of the lever 105, the pellets 3 from the next barrel 2 can be injected in the manner described. The feed motion of the magazine 1 can be realized in known manner mechanically, pneumatically, electrically and/or in another manner (the same applies to the actuation of the plunger 101).

Figure 7:
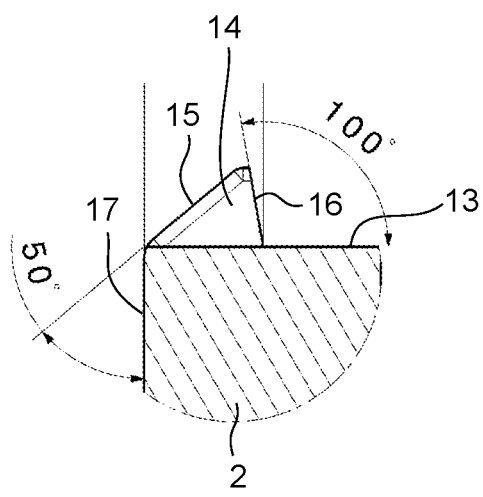
FIG. 7 is an enlarged view of detail B of FIG. 5.

The cover 9 can be held in its closed position shown in FIG. 6 by means of a detent connection. For this, several detents 14, which in each case comprise a guide surface 15 and a stop surface 16, as can be seen from FIGS. 5 to 7, are formed on the edge 13 of the end plate 7. The guide surface 15 is here inclined at an angle of 50° relative to the top side 17 of the end plate 7. The stop surface 16 is here inclined at an angle of 100° relative to the edge 13 or the longitudinal direction of the compartments 4.

Figure 8:
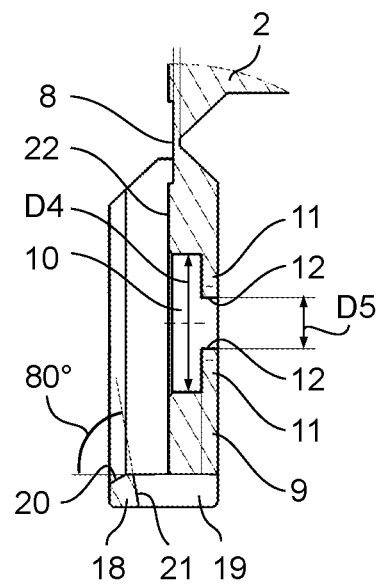
FIG. 8 is an enlarged view of detail C of FIG. 5.
Figure 9:
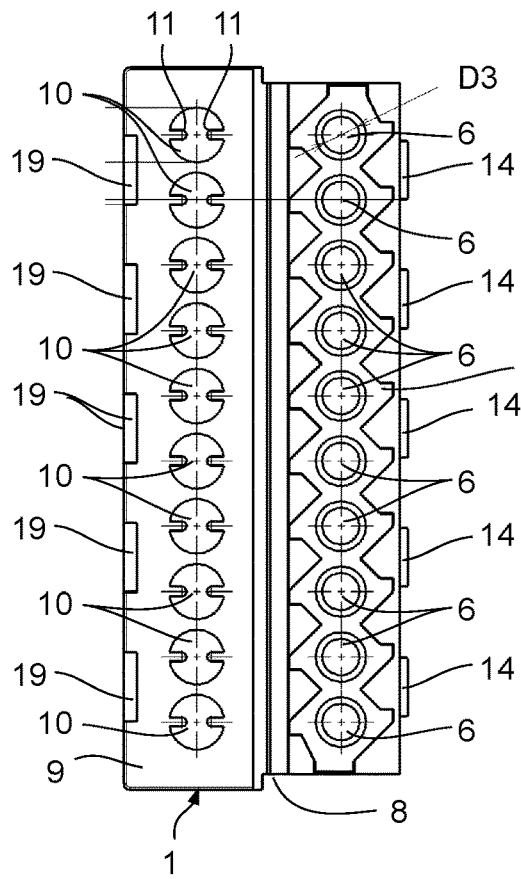
FIG. 9 is a view from below of the magazine according to the invention with opened cover.

The cover 9 comprises an edge 18, in which for each detent 14 (or detent nose 14) an associated detent recess 19 is formed, as can be seen in the enlarged detail C in FIG. 8. Each detent recess 19 comprises a sliding surface 20 and a detent surface 21. The sliding surface 20 here forms an angle of 80° with the longitudinal direction of the compartments 4. During the closing of the cover 9 (folding of the cover 9 about the hinge 8) the sliding surface 20 slides along the guide surface 15 until it reaches the stop surface 16. At this point the desired catching is then achieved, in which the detent surface 21 lies against the stop surface 16. This is possible because the cover 9 has a certain elasticity and the desired catching can thus be achieved by pressing. The thus-closed cover 9 is secured against accidental opening and, because of the bars 11 in the dispensing openings 10, it is ensured that the pellets 3 cannot accidentally fall out of the hollow cylindrical compartments 4. In the closed position of the cover 9, the underside 22 of the cover 9, from which the edge 18 projects, lies against the upper side 17 of the end plate 7.

The magazine 1 according to the invention can in particular be formed in one piece. Furthermore, the magazine 1 according to the invention can be formed from a plastic material. For example polypropylene can be used as plastic material.

As the cover 9 is connected to the barrels 2 via a hinge 8, it is ensured that the cover 9 cannot become lost. The cover 9 is thus connected to the barrels 2 in such a way that it cannot be lost. The outer contour of the barrels 2 is selected such that the described guiding and the described transport of the magazine 1 in the injector 100 is made possible.

The injector 100, which can also be called the implanter, together with the magazine 1 according to the invention forms an injector 100 according to the invention.

The injector according to the invention can optionally also comprise the needle drawer 106 described below, which serves to store a replacement hollow-bore needle 102. The needle drawer 106 is shown in its retracted position in FIG. 2 and in its partially extended position in FIG. 10, wherein in FIG. 10 only a rear housing shell 107 of the housing 108 of the injector 100 is shown. The housing 108 can also be called the main part 108. An upper and a lower guide bar 109, 110 are provided in the rear housing shell 107 for guiding the drawer 106. In the front housing shell, which is not shown, an upper and lower guide bar can be provided in the same way, which is not the case, however, in the embodiment described here. Furthermore, at least in one of the two housing shells 107, a guide recess 111 is formed into which a side knob 112 projects. In the embodiment described here, in both housing shells 107 a guide recess 111 is formed in each case, into which two side knobs 112, 113 project (FIGS. 2, 10 to 12). The knobs 112, 113 can project laterally beyond the housing 108. The knobs 112, 113 can be enclosed e.g. between thumb and index finger and the drawer 106 can then be pushed from the accommodation position according to FIG. 2 to the dispensing position.

Furthermore, the drawer 106 comprises a guide pin 114 protruding downwards which, in the embodiment shown here, lies laterally against the lower guide bar 110 and is guided by the latter.

Figure 14:
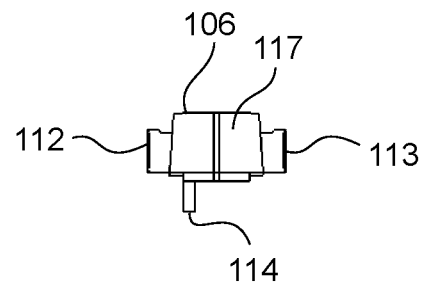
FIG. 14 is a view of the rear end of the drawer.

The drawer 106 comprises an undivided accommodation area 115 which is dimensioned such that a hollow-bore needle 102 can be accommodated as a replacement. In the embodiment described here, in the area of the bottom 118 (here as part of the bottom 118) of the accommodation area 115, a spring element 116 is arranged, which is pressed downwards when the hollow-bore needle 102 is accommodated and the drawer 106 is pushed in. This is brought about here by the upper guide bar 109, which presses the spring element 116 downwards (in the direction of the bottom 118) via the replacement hollow-bore needle (not shown) placed in the drawer 106. When the drawer 106 is pulled out backwards the thus-produced spring pretension then has the effect that the needle is raised up slightly by the spring 116, with the result that the user can easily take the replacement needle 102 out of the drawer. In the representations of FIGS. 10 and 14 the drawer is shown without a replacement needle in each case.

Thus, in the case of the injector 100 according to the invention, a replacement needle 102 can always be carried in a secure manner, with the result that during use of the injector 100, even if the needle 102 currently being used is broken off, this does not result in the use of the injector 100 having to be interrupted for long. The replacement needle need only be removed from the drawer 106, the broken-off needle 102 replaced, and the desired injections can be continued.

The drawer 106 comprises a rear end 117 which, on the one hand, delimits the accommodation area 115 and, on the other hand, is formed such that it closes the opening for the drawer 106 provided in the housing 108 flush with the rest of the housing when the drawer 106 is closed. It can also be mentioned that the rear end 117 has a shape which corresponds to the shape of the housing 108 in the area of the drawer opening.

The housing 108 and/or the drawer 106 can be formed from plastic material.

The described injector 100 with the drawer 106 can also be formed such that it can be equipped with already-known magazines. Known injectors can thus be modified such that they comprise the drawer 106 according to the invention.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An injector for injecting a pellet via a hollow-bore needle, comprising:
    a main body;
    a delivery opening formed in the main body to which the hollow-bore needle can be connected;
    a magazine for accommodating a plurality of pellets, the magazine comprising a several barrels, wherein each of the several barrels comprises a hollow cylindrical compartment with an open front end and an open rear end that can accommodate one of the plurality of pellets;
    a magazine guide configured to bring each of the several barrels of the magazine, barrel-by-barrel, into an injection position,
    wherein when a barrel of the several barrels is in the injection position, a plunger of the injector can be moved in a direction of the delivery opening in order to deliver the one of the plurality of pellets that can be accommodated in the barrel via the delivery opening; and
    a slide-out drawer formed in the main body to accommodate a replacement hollow-bore needle, the drawer comprising a sliding compartment defined by a bottom, a rear end extending upward from the bottom, a pair of sidewalk extending forward from the rear end and an open top side,
    wherein the drawer defines an undivided interior compartment that is elongated such that the replacement hollow-bore needle can fit completely within the undivided interior compartment of the drawer and be oriented parallel to a longitudinal length of the hollow-bore needle that is connected to the delivery opening.

2. The injector according to claim 1, wherein in a pushed-in state, the drawer slides into the main body such that a rear surface of the rear end of the drawer closes flush with the main body.

3. The injector according to claim 2, wherein the drawer comprises a spring element which, when the drawer is pulled out, raises the replacement hollow-bore needle situated in the drawer with respect to the bottom of the drawer.

4. The injector according to claim 3, wherein the spring element is a cantilevered-type spring.

5. The injector according to claim 3, wherein the spring element is formed as a part of the bottom.

6. The injector according to claim 1, wherein the drawer comprises a spring element which, when the drawer is pulled out, raises the replacement hollow-bore needle when the replacement hollow-bore needle is situated in the drawer with respect to the bottom of the drawer.

7. The injector according to claim 6, wherein the spring element is arranged in an area of the bottom.

8. The injector according to claim 6, wherein the spring element is formed as a part of the bottom.

9. The injector according to claim 1, wherein the drawer includes a knob extending laterally from one of the pair of sidewalls such that the knob is exposed external to the main body.

10. The injector according to claim 1, wherein a guide bar is formed in the main body to guide the sliding movement of the drawer.

11. The injector according to claim 1, wherein the drawer is configured to be slid out of the main body in a direction away from the delivery opening.

12. The injector according to claim 1, wherein the drawer is configured to accommodate several replacement hollow-bore needles.

13. The injector according to claim 1, wherein a securing element is provided to secure the drawer in a pushed-in state against an accidental moving out.

14. The injector according to claim 13, wherein the securing element is configured such that by pressing on the drawer in a direction of the main body the securing element releases the drawer.

15. The injector according to claim 14, wherein releasing of the drawer by the security element is carried out such that the drawer is at least partially slid in an outward direction from the pushed-in state.

16. The injector according to claim 1:
wherein the injector comprises the magazine inserted into the magazine guide, and the magazine is configured such that a cross-section of the hollow cylindrical compartment and of the open front end is selected such that a pellet to be accommodated can be accommodated, and a cross-section of the open rear end is smaller than the one of the plurality of pellets that can be accommodated such that the one of the plurality of pellets that can be accommodated cannot be extracted from the hollow cylindrical compartment via the rear end,
wherein the magazine further comprises a cover to close the open front end, wherein the cover comprises a dispensing opening which, in the closed state, is positioned in front of the open front end and has a cross-section selected such that the one of the plurality of pellets that can be accommodated can pass through the dispensing opening, and
wherein a bar is provided which projects into the dispensing opening to prevent the one of the plurality of pellets that can be accommodated from accidentally falling out and, when subjected to a predetermined force, can be bent outwards such that the one of the plurality of pellets that can be accommodated can be delivered through the dispensing opening.

17. The injector according to claim 1, wherein a guide pin extends below the bottom of the drawer.

18. The injector according to claim 1, wherein the rear end is shaped to correspond to the shape of the housing in the area of the drawer opening.

19. An injector system for injecting a pellet via a hollow-bore needle coupled to a delivery opening defined in a main injector body, comprising:
a magazine that can be coupled to the main injector body and accommodate a plurality of pellets, the magazine comprising several barrels, wherein each of the several barrels comprises a hollow cylindrical compartment with an open front end and an open rear end that can accommodate one of the plurality of pellets;
a magazine guide defined in the main injector body that guides the several barrels of the magazine sequentially into an injection position aligned with the delivery opening;
a plunger disposed within the main injector body that can be moved in a longitudinal direction toward the delivery opening in order to eject the one of the plurality of pellets that is accommodated in the barrel via the delivery opening;
a drawer recess defined into the main injector body; and
a drawer slidably disposed within the drawer recess,
wherein the drawer comprises:
a bottom surface;
a rear end surface extending upward from the bottom surface, and
a pair of sidewalls extending forward from the rear end surface in the longitudinal direction and extending upwards from the bottom surface,
wherein the bottom surface, the rear end surface and the pair of sidewalls together define a replacement hollow-bore needle storage compartment within the drawer such that an undivided longitudinal length dimension of the storage compartment in the longitudinal direction is greater than a width of the rear end surface in a lateral direction.

20. The injector system of claim 19, wherein the drawer recess is arranged within the main injector body such that the drawer slides linearly into and out from the injector main body parallel to a longitudinal axis of the plunger.

* * * * *